United States Patent [19]

Han et al.

[11] Patent Number: 4,987,125
[45] Date of Patent: Jan. 22, 1991

[54] ANTITHROMBOTIC ACTIVITY OF THE TRITERPENOIDS OF ILEX PUBESCENS AND THE CONVERSION METHOD OF THE TRITERPENOIDS OF ILEX PUBESCENS HAVING NO ANTITHROMBOTIC ACTIVITY INTO THE TRITERPENOIDS HAVING ANTITHROMBOTIC ACTIVITY

[75] Inventors: Yong N. Han; Byung H. Han; Soung K. Baik; Tae H. Kim, all of Seoul, Rep. of Korea

[73] Assignee: Cheil Sugar & Co., Ltd., Seoul, Rep. of Korea

[21] Appl. No.: 213,232

[22] Filed: Jun. 29, 1988

[51] Int. Cl.$^5$ ...................... A61K 31/70; A61K 31/19
[52] U.S. Cl. ..................................... 514/33; 514/557; 514/574; 536/18.1
[58] Field of Search ................. 536/18.1; 514/33, 557, 514/574; 560/116; 424/195.1

[56] References Cited

FOREIGN PATENT DOCUMENTS 2584726  1/1987  France ............................... 536/18.1
146600   9/1983  Japan ................................. 536/18.1

OTHER PUBLICATIONS

Zeng et al., "Chemical Structure of Ilexoside A", Chem. Abs., 101, 226825p (1984).
Qin et al., Chem. Abs., 94, 109171y (1981).
Qin et al., Chem. Abs., 94, 20292r (1981).
Peking Institute of Pharmaceutical Industries, Chem. Abs., 94, 114380v (1981).
Qin et al., Chem. Abs., 95, 12637n (1981).
Peking Institute of Pharmaceutical Industry, Chem. Abs., 95, 138448v (1981).
Zhang et al., Chem. Abs., 96, 196519a (1982).
Lin et al., "Crystal and Molecular Structure of Glaberide I", Chem. Abs., 97, 52551c (1982).
Qin et al., Chem. Abs., 107, 4283v (1987).
Hidaka et al., Chem. Abs., 107, 64712u (1987).
Hidada et al., Chem. Abs., 108, 52747s (1988).
Xu et al., Chem. Abs., 98, 113585m (1983).
Zeng et al., Chem. Abs., 98, 157840v (1983).
*Archives of Pharmacal Research*, Yong Nam Han et al., "Antithrombotic Activities of Saponins from Iles Pubescens," Jun. 1987, p. 115.
*Archives of Pharmacal Research*, Yong Nam Han et al., "Triterpenoids of Ilex Pubescens," Jun. 1987, p. 121.
*Archives of Pharmacal Research*, Yong Nam Han et al., "New Triterpenoid Saponins from Ilex Pubescens," Jun. 1987, p. 132.

*Primary Examiner*—John W. Rollins
*Attorney, Agent, or Firm*—Birch, Stewart, Kolasch & Birch

[57] ABSTRACT

A method of preparing a triterpenoids from Ilex pubescens which includes extracting the Ilex pubescens roots with organic solvent to an initial extract and converting the initial extract to the triterpenoids exhibiting antithrombotic activity on humans or mammals. Also, a pharmaceutical composition containing an effective antithrombotic amount of the triterpenoids from the Ilex pubescens.

7 Claims, 1 Drawing Sheet

ANTITHROMBOTIC ACTIVITY OF THE TRITERPENOIDS OF ILEX PUBESCENS AND THE CONVERSION METHOD OF THE TRITERPENOIDS OF ILEX PUBESCENS HAVING NO ANTITHROMBOTIC ACTIVITY INTO THE TRITERPENOIDS HAVING ANTITHROMBOTIC ACTIVITY

BACKGROUND OF THE INVENTION

1. Field of the Invention

The present invention relates to a novel pharmaceutical triterpenoids from Ilex pubescens exhibiting antithrombotic activity on humans and mammals and a conversion method of the triterpenoids from Ilex pubescens which have non-effective antithrombotic activity into the triterpenoids which have effective antithrombotic activity.

A mechanism of a platelet agglutination has been examined by the studies on the thromboxane $A_2(TXA_2)$ and prostacycline $I_2(PGI_2)$. The platelet agglutination is accelerated by $TXA_2$ released from platelet. On the other hand, the platelet agglutination is inhibited by $PGI_2$ released from the blood vessel. Namely, $TXA_2$ and $PGI_2$ are antagonized each other to maintain the homeostasis of the vascular system (B. Samuelsson, M. Goldyne, E. Granstrom, M. Hamberg, S. Hammarstrom, Malmsten, Prostaglandins and thromboxanes, *Ann. Rev. Biochem.* 47, 99(1978). The platelet agglutination acts an important role in the geriatric diseases; cardiovascular disease, thromboangitis obliterans, coronary disease, cerebral thrombosis, hypercholesteremia, etc.

The present invention was performed the bleeding time measurement of rats after each one of Ilex pubescens, curcumae rhizoma, Cnidii rhizoma, Angelica koreana Maximowicz, Angelicae dahuricae radix, Salvia miltriorrhiza Bunge carthami flos and Aralia cordata Thunberg was orally administered.

The above herb medicines are all related to the "blood" in chinese medicine. As a result, only the Ilex pubescens prolongs the bleeding time. Therefore, the antithrombotic compositions of the Ilex pubescens is examined.

2. Description of the Prior Art

The root of Ilex pubescens Hook. et Arn. (Aquifoliaceae), mao-dong-quing, is widely used in china for the treatment of cardiovascular disease, thromboangitis obliterans, coronary disease, cerebral thrombosis, hypercholesteremia, etc. ("Directory of Chinese Materia Medica", (Zhong Yao Da Ci Dian) ed. by Jiangsu New Medical College, Shanghai Scientific and Technological Publisher, Shanghai, p441 (1977)). The root is known to contain flavonoid glycosides (Zhang, X., Ke, M. and Ou, F.: Extraction and isolation of total flavonoid glycosides of Mao Dong Quing (Ilex pubescens) bark. *Ahongcaovao*, 12, 399 (1981); C. A. 96, 196519a(1982) and Xu, J. and Cheng, B.: Reaction between ammonium hydroxide-calcium chloride and flavones and its application. Zhongcaoyao, 13, 502 (1982); C. A. 98, 157840v (1983)) and ilexolide A (3-O-D-xylofuranosyl 18-dehydro-30-epiursolic acid (Zeng, L. M., Su, J. Y. and Zhang, S.: chemical structure of ilexolide A.: C. A. 101, 226825p (1984)). These compounds are reported to be active principles of the plant.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF PREFERRED EMBODIMENT

Figure 1:
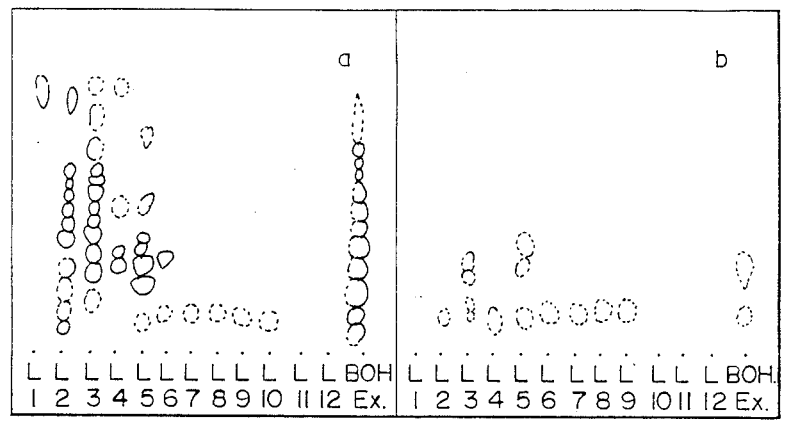
FIG. 1 illustrates thin layer chromatogram of fractions divided by column chromatography of butanol extract of Ilex pubescens by use of Cephadex LH - 20 (solvent: chloroform/methanol/$H_2O$ (70:30:4), development: a. 10% $H_2SO_4$, b. $FeCl_3$)
Figure 2:
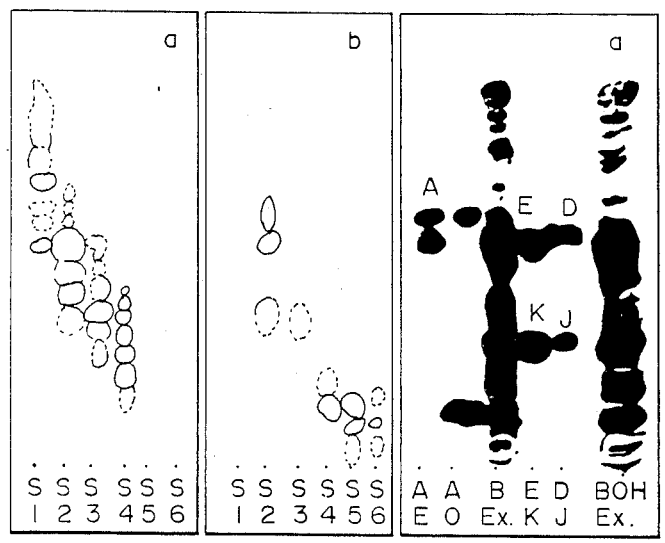
FIG. 2 illustrates thin layer chromatogram of fractions divided by silica gel column chromatography of butanol extract of Ilex pubescens (solvent: chloroform/methanol/$H_2O$ (60:40:4), development: a. 10% $H_2SO_4$, b. $FeCl_3$, Ilexoside A,D,E,J,K and)).

The present invention relates to a method for preparing antithrombotic triterpenoids on humans and mammals by administering effective amount of triterpenoids exhibiting antithrombotic activity and a method of preparing triterpenoids from Ilex pubescens exhibiting non-effective antithrombotic activity into the triterpenoids exhibiting antithrombotic activity on humans or mammals.

The present invention is provided with a comparison of bleeding times of a test group with that of a control group. To the test group, the extract of Ilex pubescens is administered with vitamin K to screen the anticoagulant effect of coumarin. The bleeding time of the test group is significantly prolonged. And then, the plasma of same rats is sampled and the coagulation time of the plasma is measured to confirm it. The coagulation time of the plasma is not changed significantly. Therefore, the prolongation effect of the bleeding time by Ilex pubescens is proposed to be caused by the inhibition of the platelet agglutination.

A platelet is agglutinated by the stimulus on thrombin. $TXA_2$ is released by this stimulation, and it accelerated the agglutination of the platelet. And the malondialdehyde(MDA) is released with $TXA_2$. It is conducted whether the extract of the Ilex pubescens inhibits the production of MDA (Determination of Melondialdehyde) or not by the colorimetry method. As the extraction solvent, methanol, butanol and water are used. When butanol is used, most part of the inhibitor for MDA production is extracted. Therefore, Sephadex LH-20 column chromatography is selected as it is known to separate the flavonoid glycosides from other components in butanol extract. As a result, the effective components are proposed to be saponins and not to be flavonoid glycosides. Their structures are as follows:

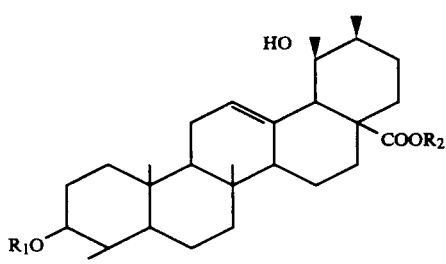

|  | R₁ | R₂ |
|---|---|---|
| Pubescenolic acid (new compound) | H | H |
| Ilexoside A | β-D-Xyl | β-D-Glu |
| Ilexoside D | β-D-Glu(1 →2)-β-D-Xyl | H |
| Ilexoside J | α-L-Rha(1 →2)-β-D-Glu(1 →2)-β-D-Xyl | H |
| Ilexoside K | β-D-Glu(1 →2)-β-D-Xyl | β-D-Glu |
| Ilexoside O | α-L-Rha(1 →2)-β-D-Glu(1 →2)-β-D-Xyl | β-D-Glu |

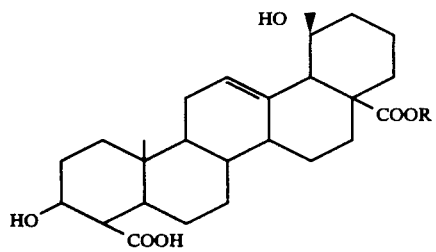

| Pubescenic acid (New compound) | R = H |
| Ilexoside E | R = Glu |

Then, the inhibition effects of MDA production by ilexosides are tested in order to examine which ilexoside inhibits MDA production. As a result, ilexoside A, ilexoside D, ilexoside J and pubescenic acid inhibits MDA production. But, ineffective ilexoside E, ilexoside K and ilexoside O are converted to effective pubescenic acid, ilexoside D and ilexoside J, respectively, by eliminating the combined saccharides on $C_{28}$-OOH.

The present invention also involves the method of converting the ineffective Ilexosides into the antithrombic Ilexosides by simple alkaline treatment.

The ineffective ilexosides (ilexoside E, ilexoside K, ilexoside O) are let stand at room temperature or heated for 0.5 to 24 hours in the solution comprising the alkaline solvent of pH 9-13 (e.g. hydroxide, carbonate or hydrogencarbonate of alkali metal; hydroxide of alkali earth metal; or ammonium hydroxide) and ethanol (1:1). It is preferable that the reaction is done under nitrogen atmosphere. After evaporating the ethanol solvent, pH of the reaction mixture is adjusted to 3-4. Then the reaction mixture is extracted by butanol, and the butanolic phase is washed with water.

Therefore, the present invention also relates to the preparation of the new ilexosides which have the antithrombic activities.

The present invention will now be described in more detail in connection with the following tests and examples which should be considered as being exemplary and not limiting the present invention.

(A) Determination of the antithrombic activities of the herb medicines (1) Determination of the bleeding time Male Sprague-Dawley rats, weighing 180–200 g, were used in experiment. One group consisted of 10 rats. The sample was prepared as follows: 100 g of roots of Ilex pubescens where extracted with 70% methanol by refluxing for 5 hours in water bath. After evaporating methanol, the residual methanol extracts were suspended in 1% CMC solution to the volume of 100 ml. Vitamin K (3 mg/kg) was added to the suspension of methanol extracts to prevent the impurities (e.g. coumarin) from prolonging the bleeding time.

To the experimental group, the suspension containing the methanol extracts (5 g of crude preparation/kg) and vitamin K was orally administered one time per day for 10 days. While, the suspension containing only vitamin K was administered to the control group by the same method.

The bleeding time was determined by the Hornstra's method: After 10 days, the rats were anesthetized by the intraperitoneal injection of sodium pentobarbital solution (50 mg/kg). The tail of the anesthetized rat was cut in the length of 5 mm and the cut tail was steeped in normal saline solution (0.9% NaCl) maintaining the temperature of 37° C. The duration time from cutting the tail to hemostasis was measured. The results are shown in Table I.

TABLE I

The effect of methanol extract of Ilex pubescens to the bleeding time in rats.

| Bleeding Time Control Group* | (sec.) Experimental Group** |
|---|---|
| 24 | 120 |
| 20 | 85 |
| 20 | 166 |
| 90 | 210 |
| 85 | 117 |
| 28 | 159 |
| 20 | 159 |
| 60 | 23 |
| 29 | 89 |
| 50 | 155 |
| 42.6 + 25.8 | 122.5 + 49.9 |

*3 mg/kg of Vitamin K was orally administered 1 time per day, for 10 days.
**5 g/kg of crude preparation (as methanol ex.) and 3 mgkg of Vitamin K were orally administered 1 time per day, for 10 days.

(2) Determination of plasma clotting time

Plasma clotting time was determined by measuring the plasma recalcification time. Plasma was prepared as follows: The rats were anesthetized with ether 24 hours after the bleeding time was measured, and the 1ml of blood was collected by heart puncture with 0.1 volume of 3.13% sodium citrate. Combined blood samples were centrifuged (3000 r.p.m. for 25 minutes; Sovall RT 6000 refrigerated centrifuge) to obtain the citrated plasma. 100 µl of citrated plasma was added to the test tube containing the 100 µl of normal saline. To it, 50 µl of 50 mM CaCl$_2$ was added and vortexed at 37° C. The elapsed time from adding CaCl$_2$ to observing the fibrin was measured. The results are shown in Table II.

TABLE II

The effect of methanol extract of Ilex pubescens to plasma clotting time in rats.

| Plasma Clotting Time Control Group* | (sec.) Experimental Group** |
|---|---|
| 146 | 112 |
| 200 | 150 |
| 364 | 248 |
| 390 | 255 |
| 235 | 162 |
| 300 | 262 |
| 210 | 206 |
| 230 | 264 |
| 162 | 390 |
| 208 | 208 |
| 244.5 + 77.4 | 225.7 + 73.9 |

*3 mg/kg of Vitamin K was orally administered 1 time per day, for 10 days.
**5 g/kg of crude preparation (as methanol ex.) and 3 mg/kg of Vitamin K were orally administered 1 time per day, for 10 days.

B. Determination of Malondialdehyde (MDA) produced by platelet (1) Determination of components by solvent fractionation of methanol extracts of Ilex pubescens.

Male Sprague-Dawley rats, weightin 180-200 g, were used in experiment. Blood was collected by the same method with (test 1-2). 100 sample was let stand for 20 minutes, in polypropylene tube. It was centrifuged (1400 r.p.m. for 20 minutes) at 10° C. to obtain platelet rich plasma (PRP). PRP was recentrifuged (2800 r.m.p., for 20 minutes) at 10° C. to obtain precipitated platelet pellet. Platelet was suspended in 0.01 M of pH 7.4 phosphate buffer ($1 \times 10^9$ cell/ml). To the platelet suspension, 100 µl of methanol extracts of Ilex pubescens was added and the reaction mixture was preincubated in thermostat of 37° C. for 20 minutes. 50 µl of thrombin (10 U) was then added to agglutinate the platelet, and thiobarbituric acid (TBA) was added as the couple. This reaction mixture was extracted by 2 ml of n-butanol and the n-butanol phase was separated by centrifugation (1200 r.p.m. for 10 minutes) at 30° C. The absorbance of n-butanol phase was observed by UV-spectrophotometer at 534 nm.

C. Preparation of methanol extract of pubescens.

1 kg of root of Ilex pubescens was powdered and the powder of Ilex pubescens was extracted 4 times with each 500 ml of 70% methanol by heating in water bath. Combined methanol phase was concentrated to obtain 259 g of methanol extract. 12 g of methanol extract was suspended in the small amount of water and extracted with butanol several times. Butanol fraction and water fraction were concentrated to 4.1 g and 6 g, respectively. 12 g of methanol extract of Ilex pubescens, 4.1 g of butanol fraction and 6 g of water fraction were dissolved to 20 ml of methanol solutions, respectively. 1ml of each solution was taken in test tube and methanol was removed under nitrogen atmosphere. Residue was suspended in 1ml of 0.01 M phosphate buffer. 0.1 ml of suspension was used as sample. The results are shown in Table III.

TABLE III

Inhibiton of malondialdehyde(MDA) generation by fractions obtained by solvent fractionation of methanol extracts of Ilex pubescens

| Fraction | Concentration* in incubated mixture (mg/1.15 ml) | Inhibition(%)** |
|---|---|---|
| Methanol | 60 | 91.5 |
| Butanol | 20.5 | 97.8 |
| Water | 30 | 0 |

*1 ml of washed platelet ($1 \times 10^9$ cells/ml) of rats was preincubated (37° C. for 30 minutes) with 0.1 ml of sample in 0.01 M phosphate buffer (pH 7.4, in normal saline). Then, to the agglutinated platelet, 50 µl of bovine thrombin (10 U) was added.
**MDA was determined by the method of TBA. Each value is the mean of 2 experimental values.

(2) Determination of components by Sephadex LH-20 column chromatography.

Butanol fraction exhibited the greatest inhibition effect of MDA generation from Table III. Therefore, 4.1 g of butanol fraction was dissolved in 10 ml of methanol and chromatographed on Sephadex LH-20 column (Sigma Co., 3.8×66 cm) with methanol as eluant. After the first eluate (260 ml) corresponding to the void volume of the column was eluted, the eluate was collected in test tubes at the volume of 21ml. 12 fractions were obtained.

| | |
|---|---|
| Fraction L-1 (0.20 g), | Fraction L-2(1.91 g), |
| Fraction L-3(1.45 g), | Fraction L-4(0.31 g), |
| Fraction L-5(0.31 g), | Fraction L-6(0.18 g), |
| Fraction L-7(0.06 g), | Fraction L-8(0.06 g), |
| Fraction L-9(0.04 g), | Fraction L-10(0.01 g), |
| Fraction L-11(0.02 g), | Fraction L-12(0.003 g). |

Each fraction was dissolved in 10 ml of methanol and 0.5 ml of methanol solution was taken. The solvent was evaporated under nitrogen atmosphere. The residue was suspended in 1ml of 0.01 M phosphate buffer and 0.1ml was used as sample. Inhibition of MDA generation was measured by the same method with Test 2-1).

TABLE V

Inhibition of MDA generation by fractions obtained during Sephadex LH-20 column chromatography of butanol extract of Ilex pubescens.

| Fraction | No. of Test Tube (21 ml/tube) | Dry Weight* (g) | Inhibition of MDA Generation (%) |
|---|---|---|---|
| Void Volume | 250 ml | 0 | 0 |
| L-1 | 1–6 | 0.20 | 0 |
| L-2 | 7–16 | 1.91 | 89.2 |
| L-3 | 17–22 | 1.45 | 84.5 |
| L-4 | 23–26 | 0.31 | 0 |
| L-5 | 27–36 | 0.31 | 83.6 |
| L-6 | 37–43 | 0.18 | 0 |
| L-7 | 44–45 | 0.06 | 0 |
| L-8 | 46–51 | 0.06 | 0 |
| L-9 | 52–57 | 0.04 | 0 |
| L-10 | 58–62 | 0.01 | 0 |
| L-11 | 63–66 | 0.02 | 0 |
| L-12 | 67–70 | 0.003 | 0 |

*4.1 g of butanol extract was chromatographed on Sephadex LH-20 column (3,8 × 66 cm) with methanol as eluant.
**Each fraction was dissolved in 10 ml of methanol and 0.5 ml of solution was taken. After removing the solvent, theresidue was dissolved in 1 ml of 0.01 M phosphate buffer (pH 7.4).0.1 ml of phosphate buffer solution was incubated with 1 ml ofplatelet of rats.

MDA generation was inhibited by fraction L-2, L-3 and L-5. But the fraction L-6 to L-12 containing flavonoid glycosides did not inhibit MDA generation. Therefore, it is suggested that the antithrombotic component of Ilex pubescens is not flavonoid glycosides.

To confirm it, each fraction was chromatographed by TLC (solvent: $CHCl_3/MeOH/H_2O$ (70:30:4) and the result is shown in FIG. 1.

When the developed plate was sprayed with 10% sulfuric acid, fraction L-2, L-3, L-4 and L-5 to Liebermann-Buchard's reaction proved positive. When the developed plate was sprayed with $FeCl_3$ solution, fraction L-4 to L-9 became blue. Therefore, the component which inhibited MDA generation was suggested to be saponins. Fraction L-4 to L-9 were proved to contain caffeic acid by preparative TLC.

(3) Determination of components by silica gel column chromatography.

From the result of Test 2-2), antithrombic component of Ilex pubescens was suggested to be saponins. Therefore, butanol extract of Ilex pubescens was chromatographed on silica gel column with the solvent containing $CHCl_3$, MeOH and $H_2O$ (80:20:1→60:20:2→60:30:4→60:40:10→50:50:2) as eluant. Inhibition of MDA generation by each fraction was determined by the same method with Test 2-1). The results are shown in table V. Fraction S-2, S-3, S-4 and S-5 inhibited MDA generation. When each fraction was developed on TLC plate with the solvent of $CHCl_3/MeOH/H_2O$ (60:40:4), saponins were detected on the spots of fraction S-2, S-3, S-4 and S-5.

TABLE V

Inhibition of MDA generation by fractions obtained during silica gel column chromatography of butanol extract of Ilex pubescens.

| Fraction | Dry weight* (g) | Inhibition of ** MDA Generation (%) |
|---|---|---|
| S-1 | 1.64* g | 0 |
| S-2 | 3.54* g | 70.44 |
| S-3 | 2.29* g | 19.50 |
| S-4 | 3.68* g | 63.52 |

TABLE V-continued

Inhibition of MDA generation by fractions obtained during silica gel column chromatography of butanol extract of Ilex pubescens.

| Fraction | Dry weight* (g) | Inhibition of ** MDA Generation (%) |
|---|---|---|
| S-5 | 0.83* g | 23.27 |
| S-6 | 0.30* g | 0 |

*Butanol extract of Ilex pubescens was chromatographed onsilica gel column with the solvent of $CHCl_3/MeOH/H_2O$ (60:40:4).
**Each fraction was dissolved in 30 ml of methanol, and0.3 ml of solution was taken. Solvent was removed from it andresidue was dissolved in 1 ml of 0.01 M phosphate buffer (pH 7.4).0.1 ml of sample was incubated with 1 ml of platelet of rats.

(4) Determination of isolated components

Inhibition (%) of MDA generation by the saponins of Ilex pubescens, ilexoside A, ilexoside D, ilexoside E, ilexoside J, ilexoside K, ilexoside O and pubescenic acid, was determined by the same method with Test 2-1). The results are shown in Table VI.

TABLE VI

Inhibition of MDA generation by Ilexoside derivatives.

| Component | $IC_{50}$ (mg)* |
|---|---|
| Pubescenolic acid | — |
| Ilexoside A | 0.22 |
| Ilexoside D | 0.17 |
| Ilexoside J | 0.68 |
| Ilexcside K | — |
| Ilexoside 0 | — |
| Prosapogenin A | — |
| Imidazole ** | 0.21 |
| Pubescenic acid | 0.41 |
| Ilexoside E | — |

*$IC_{50}$ (mg) is the concentration inhibiting 50% of MDAgeneration.
**Imidazole, known compound, is used as control.

Imidazole is known as the inhibitor of thromboxane synthase. $IC_{50}$ value is imidazole was 0.21 mg. Ilexoside D exhibited the greatest antithrombic activity ($IC_{50} = 0.17$ mg), but ilexoside K had no effect. Ilexoside K has additional saccharide on $C_{28}$—OH of ilexoside D. $IC_{50}$ value of Ilexoside J, which has one additional saccharide on Ilexoside D, was 0.68 mg, namely, about 4 times as great as that of ilexoside D. Ilexoside O, which has one additional saccharide on $C_{28}$—OOH of ilexoside J, exhibited no effect. Therefore, it is suggested that MDA generation is the best inhibited when the Ilexosides have two saccharides on —OH and no saccharide on $C_{28}$—OOH of pubescenolic acid. If there are 3 saccharides on $C_3OH$, the inhibition effect of MDA generation is reduced to one-fourth compared with the Ilexosides which has 2-saccharides on $C_3$—OH of pubescenolic acid. And MDA generation was not inhibited at all when the saccharides were combined on $C_{28}$—OOH of pubescenolic acid by ester bond.

While Ilexoside A comprising the saccharides on $C_3$—OH and $C_{28}$—OOH of pubescenolic acid has the $IC_{50}$ value of 0.22 mg. Prosapogenin A which has no saccharide on $C_{28}$—OOH of Ilexoside A did not inhibit MDA generation. Pubescenolic acid, aglycone, did not inhibit MDA generation.

Ineffective ilexoside K and ilexoside O were converted to effective ilexoside D and ilexoside J, respectively, by the simple alkaline treatment. Aglycone of ilexoside E was pubescenic acid and the $IC_{50}$ value of it was 0.41 mg. But ilexoside E comprising one saccharide on $C_{28}$—OOH of pubescenic acid did not inhibit MDA generation.

EXAMPLE 1

(1) Separation and isolation of saponins of Ilex pubescens.

Dried roots (30 kg) were crushed and extracted with MeOH (120×3) for 10 hours by the continuous extractor. The extracts were concentrated to dryness (7.78 kg). 1 kg of it was suspended in water and extracted with butanol to obtain 0.44 kg of butanol extract. 0.11 kg of butanol extract was chromatographed on silica gel flash column (Kiesel-gel 60, 70–230 mesh ASTM, Merck, Art 7734) (9.6×30 cm) with solvent comprising chloroform, methanol and water (80:20:1→60:20:2→60:30:4→30:20:5→10:10:4). Fraction 1 (14.4 g), Fraction 2 (31.2 g), Fraction 3 (20.2 g), Fraction 4 (32.4 g), Fraction 5 (7.30 g) and Fraction 6 (2.60 g) were obtained.

(2) Isolation of Ilexoside D

Fraction 2 (31.2 g) was chromatographed on silica gel column (Kiesel-gel 60, Merck, Art 7729) with the solvent of chloroform/methanol/water (80:20:0.6) and the eluate was chromatographed on TLC plate (precoated Kiesel-gel 60F$_{254}$ plate, Merck) with the same solvent as developer. The fraction which exhibited the R$_f$ value 0.42 was collected and recrystallized several times in methanol. 470 mg of Ilexoside D was obtained as the needle crystal.

mp:264–266° C. ($\alpha$)D23: +0.275 (conc. =0.53%, tetrahydrofuran(THF)) UV: end absorption only (MeOH), IR (cm$^{-1}$, KBr): 3400(OH), 1690(COOH), 1100–1000(glycoside) 13$_C$ NMR: refer to Table VII.

TABLE VII

13$_C$NMR data of Ilexoside A, ilexoside D, ilexoside E ilexoside J, ilexoside K and ilexoside O(C$_5$O$_5$N, 20MHz).

| Carbon | A | D | E | J | K | O |
|---|---|---|---|---|---|---|
| 1 | 39.1 | 39.1 | 39.0 | 39.1 | 39.1 | 38.9 |
| 2 | 26.8 | 26.8 | 28.0 | 26.9 | 26.8 | 26.6 |
| 3 | 89.0 | 89.1 | 78.3 | 89.8 | 89.2 | 90.0 |
| 4 | 39.7 | 39.7 | 49.0 | 39.8 | 39.7 | 39.8 |
| 5 | 56.2 | 56.2 | 56.2 | 56.3 | 56.1 | 56.3 |
| 6 | 18.8 | 18.8 | 20.1 | 18.9 | 18.9 | 18.8 |
| 7 | 33.5 | 33.8 | 33.0 | 33.7 | 33.6 | 33.5 |
| 8 | 40.6 | 40.5 | 39.8 | 40.5 | 40.5 | 40.6 |
| 9 | 47.9 | 47.9 | 46.7 | 47.9 | 47.9 | 47.9 |
| 10 | 37.2 | 37.2 | 37.2 | 37.3 | 37.1 | 37.2 |
| 11 | 24.1 | 24.1 | 23.7 | 24.2 | 24.1 | 24.2 |
| 12 | 127.8 | 127.5 | 128.2 | 127.5 | 127.9 | 127.9 |
| 13 | 138.9 | 139.5 | 138.8 | 139.6 | 138.7 | 138.9 |
| 14 | 42.3 | 42.3 | 41.4 | 42.3 | 42.2 | 42.3 |
| 15 | 29.4 | 29.4 | 28.1 | 29.4 | 29.4 | 29.3 |
| 16 | 27.0 | 27.2 | 25.5 | 27.3 | 27.1 | 27.0 |
| 17 | 48.5 | 48.1 | 47.8 | 48.1 | 48.4 | 48.5 |
| 18 | 47.3 | 47.6 | 53.5 | 47.6 | 47.3 | 47.4 |
| 19 | 73.7 | 73.7 | 73.1 | 73.7 | 73.7 | 73.7 |
| 20 | 42.9 | 43.1 | 41.4 | 43.1 | 42.6 | 42.8 |
| 21 | 24.7 | 25.1 | 26.3 | 25.0 | 24.7 | 24.7 |
| 22 | 31.9 | 32.5 | 36.8 | 32.6 | 31.8 | 31.8 |
| 23 | 28.4 | 28.3 | 23.5 | 28.6 | 28.3 | 28.6 |
| 24 | 17.6 | 17.4 | 176.0 | 17.5 | 17.5 | 17.6 |
| 25 | 15.8 | 15.7 | 12.8 | 15.7 | 15.8 | 15.7 |
| 26 | 17.1 | 16.9 | 16.5 | 16.9 | 16.8 | 16.9 |
| 27 | 24.4 | 24.5 | 24.0 | 24.4 | 24.5 | 24.4 |
| 28 | 177.2 | 180.8 | 176.6 | 180.8 | 177.2 | 177.2 |
| 29 | 29.9 | 29.9 | 28.3 | 29.9 | 29.9 | 29.8 |
| 30 | 16.2 | 16.3 | 16.2 | 16.4 | 16.2 | 16.2 |
| C$_{24}$COCH$_3$ | — | — | 50.3 | — | — | — |

| Methylglycoside* | A | D | E | J | K | O |
|---|---|---|---|---|---|---|
| $\beta$-D-Xylose | | | | | | |
| 1 | 106.1 | 107.4 | 105.6 | | 105.8 | 105.4 | 105.8 |
| 2 | 74.6 | 75.4 | 83.1 | | 79.5 | 82.6 | 79.4 |
| 3 | 78.1 | 78.3 | 78.2 | | 77.7 | 77.8 | 77.7 |
| 4 | 70.9 | 71.2 | 71.0 | | 71.3 | 70.9 | 71.3 |
| 5 | 66.9 | 66.9 | 66.6 | | 66.7 | 66.6 | 66.5 |
| $\beta$-B-Glucose | | | | | | |
| 1 | 105.4 | 105.8 | 102.3 | 105.6 | 102.4 | |
| 2 | 74.8 | 76.8 | 79.4 | 76.5 | 79.2 | |
| 3 | 78.1 | 78.1 | 78.8 | 77.8 | 78.9 | |
| 4 | 71.4 | 71.9 | 72.7 | 71.7 | 72.9 | |
| 5 | 78.1 | 78.1 | 78.8 | 77.8 | 78.9 | |
| 6 | 62.5 | 62.9 | 63.4 | 62.7 | 63.4 | |
| $\alpha$-L-Rhamnose | | | | | | |
| 1 | 102.4 | 101.9 | 101.9 | | | |
| 2 | 71.9 | 72.3 | 72.4 | | | |
| 3 | 72.5 | 72.6 | 72.6 | | | |
| 4 | 73.6 | 74.3 | 74.3 | | | |
| 5 | 69.4 | 69.5 | 69.5 | | | |
| 6 | 18.4 | 18.9 | 18.9 | | | |
| $\beta$-D-glucose, C$_{28}$ | | | | | | |
| 1 | 105.4 | 95.9 | 95.8 | 95.7 | 95.8 | |
| 2 | 74.8 | 74.1 | 73.9 | 73.9 | 74.2 | |

TABLE VII-continued

| | 13$_C$NMR data of Ilexoside A, ilexoside D, ilexoside E ilexoside J, ilexoside K and ilexoside O(C$_5$O$_5$N, 20MHz). | | | | |
|---|---|---|---|---|---|
| 3 | 78.1 | 78.9 | 78.7 | 78.7 | 78.8 |
| 4 | 71.4 | 71.4 | 71.3 | 71.3 | 71.4 |
| 5 | 78.1 | 78.9 | 78.7 | 78.7 | 78.8 |
| 6 | 62.5 | 62.5 | 62.5 | 62.5 | 62.5 |

*cited from J. Amer. Chem. Soc. 100, 3331 (1978).

(3) Isolation of Ilexoside E

The eluate excluding the fraction used for isolation of ilexoside D was chromatographed on silica gel column with eluant containing CHCl$_3$, MeOH and water (30:10:1).

The fraction of R$_f$ 0.4 was collected and chromatographed on silica gel column with ChCl$_3$/MeOH/water (30:10:1) and ethylacetate/MeOH/water (50:5:4), sequentially. 2.62 g of Ilexoside E, R$_f$ 0.33 on TLC palte with the solvent of ethylacetate/MeOH/water (50:5:4), was obtained as powder.

UV: end absorption only (MeOH)
IR (cm$^{-1}$, KBr):3400(OH), 1725(ester), 1690(COOH), 1100–1000 (glycoside)

1$_H$ NMR (CD$_3$OD/CDCl$_3$=1:1, TMS) δ ppm:0.77, 0.88,1.28, 1.37(5×3H, each s, 5×CH$_3$), 0.95(3H, d, J=7.0Hz, C$_{30}$—H), 2.52(1H, br.s, C$_{18}$—H), 3.10(1H,dd, J=4.8, 11.9Hz, C$_3$—H), 5.32(1H, m, C$_{12}$—H), 5.32(1H, d, J=6.6Hz, anomeric H of C$_{28}$-D-glucose)

13$_C$ NMR:refer to Table VII.

(4) Isolation of Ilexoside A 2 g of eluate excluding ilexoside D and ilexoside E was methylated by treating with diazomethane and chromatographed on silica gel flash column with the solvent of chloroform/methanol(10:1). The fraction of F$_f$0.1 on TLC plate with the solvent of chloroform/methanol (6:1) was chromatographed on silica gel column with the same solvent. 400 mg of Ilexoside A was obtained.

mp:212–214° C.
(α) D23+0.059 (conc. =0.91%, THF)
UV:end absorption only (MeOH)
IR (cm$^{-1}$, KBr):3400(OH), 1735(ester), 1100–1000 (glycoside)

1$_H$ NMR (CD$_3$OD, TMS) δ p.p.m.:2.73 (1H, br.s, C$_{18}$—H), 4.28(1H, d, J=6.7Hz, anomeric H of D-xylose), 5.31(1H, m, c$_{12}$—H), 5.33(1H, d, J=6.7 Hz, anomeric H of C$_{28}$-D-glucose)

13$_C$ NMR:refer to Table VII.

(5) Isolation of Ilexoside J

Fraction 3 (20.2 g) obtained in Example 1-1) was crystallized in methanol and 2.5 g of crystal was prepared. The crystal was dissolved in 8 ml of pyridine and 14 ml of acetic anhydride was added for acetylation. The solution was chromatographed on silica gel column with the solvent of benzene/acetone (6:1). 800 mg of Ilexoside J acetate(Ja), R$_f$0.27 on TLC plate with benzene/acetone(4:1), was obtained. 700 mg of Ja was dissolved in 50 ml of methanol and 8.4 ml of 0.7 M K$_2$CO$_3$ was added. This solution was let stand over night, and then methanol was removed. The pH of the remaining solution was adjusted to 3–4 with 2 N sulfuric acid and it was extracted with butanol. After washing the butanol phase with water, it was recrystallized in methanol. Obtained crystal was chromatographed on silica gel flash column with chloroform/methanol/water (70:30:4). The fraction of R$_f$0.25 with the same solvent was collected and recrystallized in methanol. 120 mg of Ilexoside J was obtained.

(α)D23+0.115 (conc. = 0.27%, THF)
UV:end absorption only.
IR (cm$^{-1}$, KBr): 3400(OH), 1700(COOH), 1100–1000 (glycoside)

1H NMR (CD$_3$OD/CDCl$_3$=1:1, TMS) δ p.p.m.:0.79, 0.85, 0.94, 1.08, 1.17, 1.29(6×3H, each s, 6×CH3), 0.99( 3H, d, J=7.0 Hz, C$_{30}$—H$_3$), 1.26(3H, d, J=5.3Hz, CH$_3$ of L-rhamnose), 2.75 (1H, br.s, C$_{18}$—H), 4.30(1H, d, J=6.2 Hz, anomeric H of D-xylose), 4.79(1H, d, J=6.8 Hz, anomeric H of D-glucose), 5.18(1 H, d, J=0.9 Hz, anomeric H of L-rhamnose), 5.27(1 H, m, C$_{12}$—H).

13$_C$ NMR (pyridine-d$_5$, TMS) δ p.p.m.:refer to Table VII.

(6) Isolation of Ilexoside K

Fraction 4 (32.4 g) obtained in Example 1-1) was chromatographed on silica gel column with chloroform/methanol/water (60:30:4) and the samples of eluate were developed on TLC plate with chloroform/methanol/water (30:20:5). The fraction of R$_f$0.8 was collected and chromatographed on silica gel column with chloroform/methanol/water (70:30:4). The eluate of R$_f$ 0.4, on TLC plate with chloroform/methanol/water (30:20:5), was collected and chromatographed on Sephadex LH-20 column (Sigma Co.) with methanol. Isolated fraction was rechromatographed on silica gel column with chloroform/methanol/water (75:25:4) and 3.0 g of desired compound, R$_f$0.3 with the same solvent, was obtained.

mp:204–206° C.
(α)D23 :+0.156 (conc. = 0.57%, THF)
UV:end absorption only (MeOH).
IR (cm$^{-1}$, KBr): 3400(OH), 1735(ester), 1100–1000 (glycoside)

1$_H$ NMR (CDCl$_3$CD$_3$OD/D$_2$O/TFA=7:3:0.5:1, TMS) δ p.p.m.: 0.74, 0.83, 0.93 1.03, 1.20, 1.26(6×3H, each s, 6×CH$_3$), 0.99(3H, d, J=7.0 Hz, C$_{30}$—H$_3$), 2.80(1H, br.s, C$_{18}$—H), 4.44(1H, d, J=6.0 Hz, anomeric H of D-xylose), 4.67 (1H, d, J=6.9Hz, anomeric H of D-glucose), 5.57 (1H, m, anomeric H of C$_{28-D-glucose}$), 5.23(1H, m, C$_{12}$—H).

13$_C$ CNMR (pyridine-d$_5$):refer to Table VII.

(7) Isolation of Ilexoside O

Fraction 4 (32.4 g) obtained in Example 1-1) was chromatographed on silica gel column with chloroform/methanol/water (60:30:4) and the smaplesof eluate were developed on TLC plate with chloroform/methanol/water (30:20:5).

The fraction of R$_f$0.5(3.2 g) was collected and chromatographed on silica gel column with chloroform/methanol/water (60:30:4) and the fraction of F$_f$0.15 was collected. Collected fraction was chromatographed on Sephadex LH-20 with methanol and isolated solution was rechromatographed on silica gel column with chloroform/methanol/water (60:35:4). The fraction of $R_f$ 0.38, developed with chloroform/methanol/water (30:20:5), was collected and recrystallized in methanol. 300 mg of Ilexoside O was obtained.

mp:224–226° C.

$(\alpha)$D23 :—0.194 (conc. = 1.0%, pyridine)

UV:end absorption only (MeOH).

IR (cm$^{-1}$, KBr): 3400(OH), 1730(ester), 1100–1000 (glycoside)

$^1$H NMR (CD$_3$OD/CDCL$_3$=1:1, TMS) δ p.p.m.: 0.77, 0.84, 0.94, 107, 1.18, 1.29(6×3H, each s, 6×CH$_3$), 1.02(3H, d, J=7.0Hz, C30-H3), 1.26(3 H, d, J=5.9 Hz, CH$_3$ of L-rhamnose), 2.74(1H, br.s, C$_{18}$—H), 4.31(1H, d, J=6.7 Hz, anomeric H of D-xylose), 4.80(1H, d, J=4.8 Hz, anomeric H of D-glucose), 5.18(1H, d, J=1.3 Hz, anomeric H of L-rhamnose), 5.34(1H, d, J=6.8 Hz, anomeric H of C$_{28}$-D-glucose), 5.28(1H, m, C$_{12}$—H).

13$_C$ NMR (pyridine-d$_5$ TMS):refer to Table VII.

(8) Oxidation with HIO$_4$ and alkaline treatment of Ilexosides 130 mg of ilexoside A and 130 mg of ilexoside E were dissolved in 20 ml of methanol respectively. Each 130 mg of ilexoside D, ilexoside J, ilexoside K and ilexoside was dissolved in the solution containing 1ml of pyridine and 20 ml methanol. 200 mg of HIO$_4$.2H$_2$O was dissolved in 2 ml of water. HIO$_4$ solution was added to the above Ilexosides solutions respectively. Each reaction mixture was let stand for 2 days with stirring and cooling. To this solution, 50 μl of ethyleneglycol was added and it was suspended in 150 ml of water. 80 mg of KI was added to the suspension. Produced I$_2$ was removed by adding sodium arsenite solution till the color of I$_2$ was disappeared. After adding 10% KOH solution and ethanol in equal amount, the mixture was heated for 4 hours under nitrogen atmosphere. Organic solvents were removed from it and remaining solution was cooled. pH of solution was adjusted to 3–4 with 20% sulfuric acid and it was extracted with ethylacetate. After washing ethylacetate phase several times with wear, ethylacetate solution was concentrated. Aglycone fractions of ilexosides were obtained respectively.

Aglycone of ilexoside A was chromatographed on silica gel column with chloroform/methanol (10:1) and recrystallized in chloroform. 40 mg of pubescenolic acid ($R_f$0.44, with chloroform/methanol(8:1)) was obtained as colorless needle crystal. Pubescenolic acid was obtained from ilexoside D, ilexoside J, ilexoside K and ilexoside 0, too.

mp:256–258° C.

$(\alpha)$D23+0.48(THF)

IR (cm$^{-1}$, KBr):3620, 3480(OH), 1690(COOH), 1030, 995(C-OH), 930(tert, C-OH) $^1$H NMR (CDCl$_3$/pyridine-d$_5$, 1 drop) δ p.p.m.:0.66, 0.75, 0.87(4×3H, each s, 4×CH$_3$), 0.88(3H, d, J=6.7 Hz, C$_{30}$—H$_3$), 1.06(3H, s, C$_{27}$H$_3$), 1.18(3H, s, C$_{29}$—H$_3$), 2.79(1H, s, C$_{18}$—H), 3.09(1H, t- like, C$_3$—H), 5.23(1H, m, C$_{12}$—H) MS m/z (Rel. Int. %):472(M+, 16.7), 454(M+—H$_2$O, 14.5), 426(M+—HCOOH, 48.0), 354(14.0), 264(1.4), 207(32.3), 190(41.0), 146(100), 72(20.5).

Aglycone of ilexoside E was chromatographed on silica gel column with chloroform/methanol(8:1) and the eluate of $R_f$0.35 when developed on TLC plate by chloroform/methanol(6:1) was collected. 60 mg pubescenic acid was obtained.

mp:above 320° C.

$(\alpha)$D23:+0.672 (conc. =0.5%, THF)

UV:end absorption only (MeOH)

IR (cm$^{-1}$, KBr): 3565, 3480(OH), 1695(COOH), 1020, 995(C—OH), 930(tert, C—OH)

$^1$H NMR (CDCl$_3$/pyridine-d$_5$, 1 drop, TMS) δ p.p.m.:0.85, 0.93, 1.24, 1.33, 1.48(5×3H, each s, 5×CH$_3$), 0.94(3H, d, J=7.0dHz, C$_{30}$—H$_3$), 2.68(1H, s, C$_{18}$—H), 3.31(1H, dd, J=4.4, 11.2Hz, C$_3$—H), 5.40(1H, m, C$_{12}$—H).

MS m/z (Rel. Int. %):502(M+, 10.3), 456(M+—CO$_2$, 93.6), 384(26.3), 220(37.8), 201(23.1), 146(100), 91(80.1), 44(59.6).

EXAMPLE 2

To 100 mg of ilexoside A, 10% KOH solution and ethanol were added in equal amount. Reaction mixture was heated for 4 hours under nitrogen atmosphere and ethanol was removed. pH of solution was adjusted to 3–4 with 20% sulfuric acid and it wa extracted with butanol. Prosapogenin A fraction was obtained by washing butanol phase with water. Prosapogenin fractions of ilexoside E, ilexoside K and ilexoside O were prepared by the same method with ilexoside A.

(1) Isolation of prosapogenin A

Prosapgenin A fraction was chromatographed on silica gel column with chloroform/methanol (10:1) and the fraction of $R_f$0.21 was collected. 15 mg of prosapagenin A of ilexoside A was obtained by recrystallizing the fraction of $R_f$0.21 in methanol.

mp:157–259° C.

$(\alpha)$D23:+0.352 (conc. =0.20%, THF)

IR (cm$^{-1}$, KBr):b 3595, 3400(OH), 1690(COOH), 1100–1000(glycoside)

$^1$H NMR (CD$_3$OD/CDCl$_3$=1:1, TMS) δ p.p.m.:0.79, 0.85, 0.94, 1.05, 1.17, 1.29(6×3H, each s, 6×CH$_3$), 1.00(3H, d, J=6.8 Hz, CHd 30—H$_3$), 2.78(1H, br.s, C$_{18}$—H), 3.10(1H, m, Chd 3—H), 4.33(1H, d, J=6.7 Hz, anomeric H of D-xylose), 5.31(1H, m, C$_{12}$—H).

(2) Isolation of Prosapogenin E

Prosapogenin E fraction was chromatographed on silica gel column with chloroform/methanol(8:1) and the fraction of $R_f$0.35 (chloroform/methanol (6:1)) was collected. 50 mg of prosapogein was obtained. mp, Mass, NMR, IR and Co-TLC was corresponding to that of pubescenic acid.

(3) Isolation of prosapogenin K

Prosapogenin K fraction was chromatographed on silica gel column with chloroform/methanol/water (80:20:1) and the fraction of $R_f$ 0.4 (chloroform/methanol/water (80:20:1)) was collected. 43 mg of prosapogenin K was obtained by recrystallizing the fraction with methanol. mp, Mass, NMR, IR and Co-TLC was corresponding to that of Ilexoside D.

(4) Isolation of prosapogenin O

Prosapogenin 0 fraction was chromatographed on silica gel with chloroform/methanol/water (70:30:2) and the fraction of $R_f$0.25 (chloroform/methanol/water (70:30:2)) was collected. mp, Mass, NMR, IR and Co-TLC was corresponding to that of Ilexoside J.

EXAMPLE 3

Ilexoside A was isolated from the butanol extract of Ilex pubescens by the method of Example 1–4). Remaining solution was treated by the same method with Example 2 except using 10% NaOH solution instead of 10% KOH solution to convert ilexoside K and ilexoside O into ilexoside D and ilexoside J, respectively.

EXAMPLE 4

The same procedure described in Example 3 was repeated using 15% $Na_2CO_3$ aqueous solution instead of 10% NaOH. The mixture of ilexoside D and ilexoside J was obtained.

EXAMPLE 5

The same procedure described in Example 3 was repeated using 12% ammonium hydroxide instead of 10% NaOH. The mixture of ilexoside D and ilexoside J was obtained.

EXAMPLE 6

The same procedure described in Example 3 was repeated using 10% $Ca(OH)_2$ solution instead of 10% NaOH. The mixture of ilexoside D and ilexoside J was obtained.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A method of preparing triterpenoids from Ilex pubescens roots, said triterpenoids exhibiting antithrombotic activity on humans or mammals, the method for preparation comprising:

(a) extracting said Ilex pubescene roots with an organic solvent by heating in a water bath to produce a first extract, said first extract including said triterpenoids which are designated as ilexoside A, ilexoside D, ilexoside E, ilexoside J, ilexoside K, and ilexoside O, said ilexosides A, D, J, K, and O having 18-α-hydroxy-20-epiursolic acid which is designated as pubescenolic acid, said ilexoside E having 24-carboxypomolic acid which is designated as pubescenic acid, (b) isolating said ilexoside A from said first extract to produce a second extract, (c) hydrolyzing said ilexoside E, said ilexoside K, and said ilexoside O in said second extract with an alkaline to form said pubescenic acid, said ilexoside D, said ilexoside J to produce a third extract, and (d) isolating said pubescenic acid, said ilexoside D, and said ilexoside j from said third extract.

2. The method of preparing triterpenoids of claim 1, wherein the alkaline hydrolysis is conducted at room temperature for 0.5 to 24 hours.

3. The method of preparing triterpenoids of claim 1, wherein the alkaline material for use in the alkaline hydrolysis is a chemical selected from the group consisting of hydroxide, carbonate, bicarbonate of alkalimetal, hydroxide of alkalimetal, and ammonium hydroxide.

4. The method of preparing triterpenoids of claim 1, wherein the organic solvent is selected from the group consisting of methanol, water, and butanol.

5. A pharmaceutical composition produced by the method of claim 1.

6. A method for treating thrombosis by administering to humans an effective antithrombotic amount of triterpenoids from Ilex pubescens.

7. The method of claim 6, wherein the triterpenoids contains ilexoside D, ilexoside J, and pubescenic acid.

* * * * *